United States Patent [19]

Köppe et al.

[11] 4,344,964
[45] Aug. 17, 1982

[54] 1-(ALKANOYLAMINO-ARYLOXY)-2-HYDROXY-3-(ALKINYL-AMINO)-PROPANES AND SALTS THEREOF

[75] Inventors: Herbert Köppe; Werner Kummer; Helmut Stähle; Gojko Muacevic, all of Ingelheim am Rhein; Werner Traunecker, Münster-Sarmsheim, all of Fed. Rep. of Germany

[73] Assignee: C. H. Boehringer Sohn, Ingelheim am Rhein, Fed. Rep. of Germany

[21] Appl. No.: 241,519

[22] Filed: Mar. 9, 1981

[30] Foreign Application Priority Data

Mar. 8, 1980 [DE] Fed. Rep. of Germany ....... 3009036

[51] Int. Cl.³ .................. A61K 31/275; C07C 121/78
[52] U.S. Cl. ................................. 424/304; 260/465 D
[58] Field of Search .................... 260/465 D; 424/304

[56] References Cited

U.S. PATENT DOCUMENTS 3,925,446 12/1975 Röppe et al. .................... 260/465 E

*Primary Examiner*—Dolph H. Torrence
*Attorney, Agent, or Firm*—Hammond & Littell, Weissenberger & Muserlian

[57] ABSTRACT

This invention relates to a compound of the formula

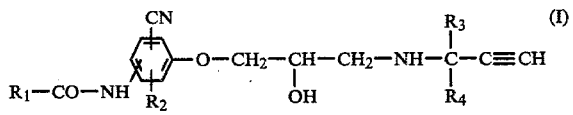

wherein
$R_1$ is ethyl or isopropyl;
$R_2$ is hydrogen, halogen, alkyl of 1 to 4 carbon atoms, alkoxy of 1 to 4 carbon atoms or a bivalent radical —CH=CH—CH=CH— or —(CH$_2$)$_n$—, where n is an integer from 3 to 5, inclusive, and the free bonds of said bivalent radical are attached to adjacent carbon atoms of the phenyl ring; and
$R_3$ is hydrogen or alkyl of 1 to 3 carbon atoms;
$R_4$ is alkyl of 1 to 3 carbon atoms; or
$R_3$ and $R_4$, together with each other, are —(CH$_2$)$_p$—, where p is an integer from 4 to 6, inclusive, or a non-toxic, pharmacologically acceptable acid addition salt thereof. The compounds of formula I are useful for treatment and prophylaxis of diseases of the coronaries, for treatment of hypertension, and for treatment of cardiac arrhythmia, particularly tachycardia.

6 Claims, No Drawings

1-(ALKANOYLAMINO-ARYLOXY)-2-HYDROXY-3-(ALKINYL-AMINO)-PROPANES AND SALTS THEREOF

This invention relates to novel 1-(alkanoylamino-aryloxy)-2-hydroxy-3-(alkinyl-amino)-propanes and non-toxic acid addition salts thereof, to methods of preparing these compounds, to pharmaceutical compositions containing them as active ingredients, and to methods of using them for the treatment of tachycardia, hypertension and disorders of the coronary vessels.

More particularly, the present invention relates to a novel class of compounds represented by the formula

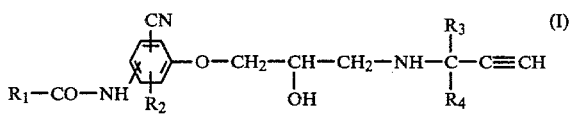

wherein
  $R_1$ is ethyl or isopropyl;
  $R_2$ is hydrogen, halogen, alkyl of 1 to 4 carbon atoms, alkoxy of 1 to 4 carbon atoms or a bivalent radical —CH=CH—CH=CH— or —$(CH_2)_n$—, where n is an integer from 3 to 5, inclusive, and the free bonds of said bivalent radical are attached to adjacent carbon atoms of the phenyl ring; and
  $R_3$ is hydrogen or alkyl of 1 to 3 carbon atoms;
  $R_4$ is alkyl of 1 to 3 carbon atoms; or
  $R_3$ and $R_4$, together with each other, are —$(CH_2)_p$—, where p is an integer from 4 to 6, inclusive,
and non-toxic, pharmacologically acceptable acid addition salts thereof.

The compounds embraced by formula I may be prepared by the following methods:

Method A.

By reacting a compound of the formula

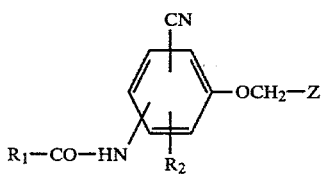

wherein
  $R_1$ and $R_2$ have the same meanings as in formula I, and
  Z is

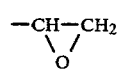

or —CH(OH)—$CH_2$—Hal, where Hal is halogen, with an amine of the formula

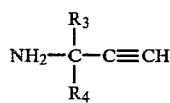

wherein $R_3$ and $R_4$ have the same meanings as in formula I.

Method B.

By hydrolyzing an oxazolidine derivative of the formula

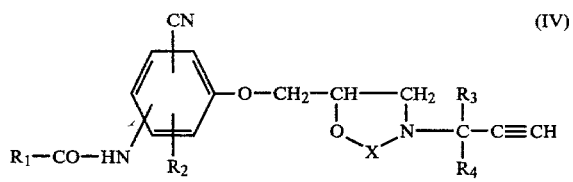

wherein
  $R_1$, $R_2$, $R_3$ and $R_4$ have the same meanings as in formula I, and
  X is —CO—, —$CH_2$— or —CH(lower alkyl)—,
with an aqueous solution of sodium hydroxide or potassium hydroxide, or with a mixture of ethanol and water.

Method C.

By reacting a compound of the formula

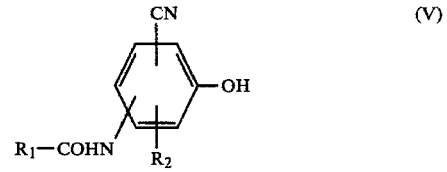

wherein $R_1$ and $R_2$ have the same meanings as in formula I, or a salt thereof, with an azetidinol derivative of the formula

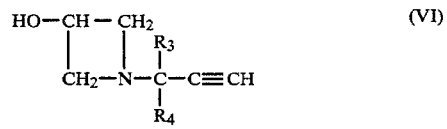

wherein $R_3$ and $R_4$ have the same meanings as in formula I, in an anhydrous medium.

The oxazolidinone starting compounds of the formula IV, i.e. those where X is —CO—, may be prepared by reacting an epoxide of the formula II with a urethane of the formula

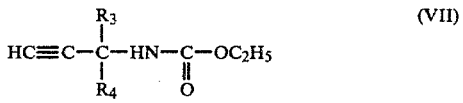

wherein $R_3$ and $R_4$ have the same meanings as in formula I.

A urethane of the formula VII is obtained by reacting ethyl chloroformate with an amine of the formula III.

The starting compounds of the formula V are known compounds and may be prepared by methods which are described in the literature.

The starting compounds of the formula VI may be prepared, for example, by the method described in Chem. Pharm. Bull. (Japan), Vol. 22(7), 1974, page 1490.

The compounds of the formula I comprise an asymmetric carbon atom in the —CH(OH)— group and therefore occur as racemates and as optical antipodes. The latter may be isolated not only by separation of the racemate with the aid of conventional auxiliary acids, such as dibenzoyl-D-tartaric acid, di-p-toluyl-D-tartaric acid or D-3-bromo-camphor-8-sulfonic acid, but also by using the corresponding optically active starting material.

The compounds of the formula I are basic and therefore form addition salts with inorganic or organic acids. Examples of non-toxic, pharmacologically acceptable acid addition salts are those formed with hydrochloric acid, hydrobromic acid, sulfuric acid, methane-sulfonic acid, maleic acid, acetic acid, oxalic acid, lactic acid, tartaric acid, 8-chlorotheophylline or the like.

The following examples illustrate the present invention and will enable others skilled in the art to understand it more completely. It should be understood, however, that the invention is not limited solely to the particular examples given below.

EXAMPLE 1

1-[2-cyano-4-(n-propionyl-amino)-phenoxyl]-3-(2-methyl-butinyl-3-amino-2)-2-propanol by method A 7 gm of 1-[2-cyano-4-(n-propionyl-amino)-phenoxy]-2,3-epoxy-propane were dissolved in 100 ml of ethanol. After addition of 7 gm of 2-methyl-butine-3-amine-2 the mixture was refluxed for two hours. After cooling, the solvent was distilled off, the residue was stirred with dilute HCl, extracted twice with 150 ml each of ethyl acetate, and the aqueous phase was separated and made alkaline with sodium hydroxide. The precipitated base was taken up in ethyl acetate, and the organic phase was washed neutral with water. After drying over Na2SO4 it was evaporated. The residue was recrystallized from ethyl acetate by addition of petroleum ether (b.p. 60° C.).

Yield: 3.4 gm of the compound of the formula

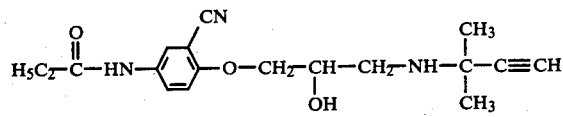

which had a melting point of 138°–139° C.

EXAMPLE 2

1-[2-cyano-6-(isobutyroyl-amino)-phenoxyl]-3-(2-methyl-butinyl-3-amino-2)-2-propanol and its oxalate by method A 8.7 gm (0.029 mol) of 1-[2-cyano-6-(isobutyroyl-amino)-phenoxy]-2-hydroxy-3-chloro-propane were dissolved in 80 ml of ethanol, and 15.5 ml (0.147 mol) of 2-methyl-butine-3-amine-2 were added. After heating the mixture for one hour under reflux the volatile components were distilled off in vacuo. The residue was taken up in 65 ml of dilute HCl, extracted twice with 50 ml each of ethyl acetate, and the aqueous phase was made alkaline with sodium hydroxide. The precipitated base was extracted three times with 75 ml each of ethyl acetate, and the organic phase was dried over sodium sulfate, suction-filtered and evaporated in vacuo. The residue was purified on a silicagel column. The fractions containing the pure substance were combined, and the mixture of solvents was distilled off in vacuo. The residue was dissolved in little acetonitrile and added dropwise to a solution of 3.5 gm of oxalic acid in 10 of acetonitrile. After addition of a little ether the oxalate crystallized out as a colorless substance. It was once more recrystallized from methanol by addition of ether.

Yield: 2.4 gm of the compound of the formula

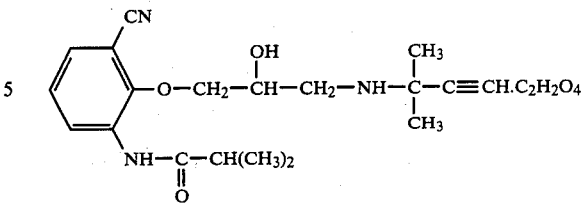

which had a melting point of 195°–196° C.

EXAMPLE 3

1-[2-cyano-4-(isobutyroyl-amino)-phenoxy]-3-(2-methyl-butinyl-3-amino-2)-2-propanol by method B 3.1 gm (0.015 mol) of 2-cyano-4-isobutyroylaminophenol were admixed with 7.2 gm (0.08 mol) of epichlorohydrin and 0.1 gm of piperidine, and the mixture was stirred for 5 hours at 100° C. After distilling off the excess epichlorohydrin the residue was dissolved in 20 ml of ethanol, 4 ml of 2-methyl-butine-3-amino-2 were added, and the mixture was refluxed for three hours. After distilling off the solvent the residue was acidified with dilute hydrochloric acid and extracted three times with ether. The aqueous phase was made alkaline with sodium hydroxide, and the precipitated amine was extracted with ethyl acetate. The organic phase was washed with water, dried over Na2SO4, and the ethyl acetate was distilled off. The residue was dissolved in ethanol, suction-filtered through charcoal and evaporated in vacuo. The residue (3.3 gm) was stirred with ether, suction filtered and washed with ether. The solid components were recrystallized from a little acetonitrile (4 ml), washed with ether and recrystallized once more from 4 ml of acetonitrile.

Yield: 1.1 gm; m.p.: 110°–111° C.

After evaporating the combined mother liquors the residue was purified on a silicagel column. By working up the fractions a solid crystallizate was obtained, which was recrystallized from acetonitrile. Another 1.3 gm of pure product having a melting point of 109.5°–111° C. were obtained.

EXAMPLE 4

1-[2-cyano-4-(isobutyroyl-amino)-phenoxy]-3-(1-ethinyl-cyclohexylamino)-2-propanol by method A 7.8 gm (0.03 mol) of 1-[2-cyano-4-(isobutyroyl-amino)-phenoxy]-2,3-epoxy-propane were dissolved in 80 ml of ethanol, and after addition of 7.5 gm (0.06 mol) of 1-ethinyl-cyclohexyl-amine the mixture was refluxed for one hour. The solvent was then distilled off, and the residue was acidified with dilute HCl. After extraction with ethyl acetate the aqueous phase was made alkaline by addition of NaOH, whereby basic components precipitated in oily form. They were taken up in ethyl acetate, the organic phase was washed with water, dried over MgSO4, evaporated and the solid residue was recrystallized twice from acetonitrile.

Yield: 4.9 gm of the compound of the formula

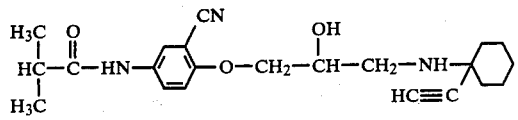

which had a melting point of 142°–144° C.

EXAMPLE 5

1-[2-cyano-4-(isobutyroyl-amino)-phenoxy]-3-(3-ethyl-pentinyl-4-amino-3)-2-propanol by method A 7.8 gm (0.03 mol) of 1-[2-cyano-4-(isobutyroyl-amino)-phenoxy]-2,3-epoxy-propane were refluxed in 100 ml ethanol with 11.1 gm (0.03 mol) of 3-ethyl-pentine-4-amine-3 for one hour. After distilling off the solvent, the residue was acidified with dilute HCl, neutral organic substances were extracted with ether, and the aqueous phase was made alkaline with NaOH. The basic components which precipitated in oily form were taken up in ethyl acetate, and the organic phase was washed with water. After drying over $Na_2SO_4$, the ethyl acetate was distilled off. The residue was recrystallized twice from ethyl acetate by addition of petroleum ether.

Yield: 5.8 gm; m.p.: 98°–99° C.

EXAMPLE 6

1-[2-cyano-4-(n-propionyl-amino)-phenoxy]-3-(2-methyl-butinyl-3-amino-2)-2-propanol by method C 6.3 gm (0.045 mol) of 1-(2-methyl-butin-1-yl-3)-3-azetidinol were dissolved in 30 ml benzyl alcohol, and 9.0 gm (0.05 mol) of 2-cyano-4-(n-propionyl-amino)-phenol and 100 mg of KOH were added while continuously stirring. The mixture was heated at 140° C. for five hours in a nitrogen atmosphere. After cooling, 70 ml of ether were added. By repeatedly shaking the solution with dilute HCl the basic components were extracted. The aqueous phase was washed with water and made alkaline with NaOH. The basic components which precipitated in oily form were taken up in ethyl acetate, washed with water and dried over $Na_2SO_4$. After distilling off the ethyl acetate the residue was recrystallized from ethyl acetate by addition of petroleum ether. The crystallizate was purified twice more in the same way.

Yield: 4.1 gm; m.p.: 137°–139° C.

EXAMPLE 7

1-[2-cyano-4-(isobutyroyl-amino)-phenoxy]-3-(2-methylbutinyl-3-amino-2)-2-propanol by method B 4.06 gm (0.01 mol) of 3-(2-methylbutine-3-amine-2)-5-[2-cyano-4-(isobutyroyl-amino)-phenoxymethyl]-oxazolidinone-2 were refluxed for half an hour in 25 ml of ethanol after addition of 2 gm of KOH in 5 ml of water. Then the solvent was distilled off, and the residue was stirred with water and extracted with ethyl acetate. The organic phase was extracted with dilute HCl, and the aqueous phase was washed with ethyl acetate and made alkaline with NaOH. The basic components which precipitated in oily form were taken up in ethyl acetate, washed with water and dried over $Na_2SO_4$. The solvent was distilled off, and the residue was recrystallized twice by addition of petroleum ether.

Yield: 1.6 gm; m.p.:109°–111° C.

The compounds of the present invention, that is, those embraced by formula I above and their non-toxic, pharmacologically acceptable acid addition salts, have useful pharmacodynamic properties.

More particularly, in the animal test on guinea pigs they exhibit β-adrenolytic properties and may therefore be used, for example, for treatment and prophylaxis of diseases of the coronaries and for treatment of cardiac arrhythmia, in particular of tachycardia. The hypotensive properties of the compounds are of therapeutic interest as well. In comparison to the known β-receptor blocker, for example, the commercial product of similar structure, 1-(2-acetyl-4-butyroylaminophenoxy-2-hydroxy-3-isopropylaminopropane (acebutolol), the compounds have the advantage of a considerably lower toxicity, a better β-isoprenaline antagonistic activity and an excellent organ selectivity. These parameters were measured by means of the following test models:

1. Inhibition of the isoprenaline tachycardia (isoprenaline antagonistic activity)

Method: Inhibition of the tachydardiac reaction to a standard dose of isoprenaline and effect upon the basal heart rate of increasing i.v. dosages of a β-adrenolytic.

Animal material: Guinea pigs of both sexes with body weights of 270–350 gm, group keeping, standard feed and water until beginning of test ad libitum. Sixteen hours before beginning of test withdrawal of nutrition.

Anesthesia: Ethylurethane 1.75 gm/kg as 20% solution intraperitoneally; if required, it was reinjected.

Preparation: Cannulation of a Vena jugularis exterior for intravenous injection: Insertion of a tracheal cannula and artificial respiration; subcutaneous needle electrodes for recording of the ECG, as a rule extremity lead II, recording rate 25 mm/sec; rectal thermometer for control of body temperature which is kept constant at 34°–36° C. by means of an infrared heat lamp controlled by an automatic electronic heat sensing device.

Test Procedure: The heart rate is determined by counting the r-waves in the ECG, each from a recording time of 3–4 seconds. About 30 minutes after the preparation the normal heart rate is recorded and averaged five times in intervals of 2 minutes. Subsequently, 1 μg/kg of isoprenaline is injected i.v. as adrenergic stimulant, and afterwards the heart rate is recorded repeatedly for 3 minutes each 3 seconds. The injections of isoprenaline are repeated during the whole time of the test at intervals of 30 minutes. If the spontaneous rate remains almost constant and if the tachycardiac reaction upon the first 2–3 isoprenaline administrations is homogeneous, then there is injected i.v. —15 minutes after the last 15 minutes before the next isoprenaline reaction—the first dose of the test compound. Further doses of the test compound increasing in geometric series follow at intervals of 60 minutes until a distinct inhibition of the isoprenaline tachycardia has been reached.

2. Test for cardioselectivity on the conscious guinea pig

Principle: According to the method of D. Dunlop and R. G. Shanks [Brit. J. Pharmacol. 32, 201 (1968)] conscious guinea pigs are exposed to a lethal dose of a histamine aerosol. by pre-treatment with isoprenaline the animals are protected from the lethal effect of the histamine. A β-adrenolytic neutralizes the isoprenaline, so that the protection against histamine bronchospasms is lost if a non-cardioselective substance is involved. If a cardiac-active β-adrenolytic substance does not show any antagonism against isoprenaline in this test, the presence of cardioselectivity (for so-called $β_1$-receptors) may be assumed.

Animal material: Guinea pigs of both sexes (6 animals per dose), with 350–400 gm body weight, group keeping. Standard feed and water until beginning of test ad libitum. Sixteen hours before beginning of test withdrawal of feed.

Test Procedure: Groups of 6 animals each (3 male and 3 female) are treated subcutaneously with 5 or more different doses of the β-adrenolytic. Fifteen minutes later they get a contralateral subcutaneous injection of 0.01 mg/kg isoprenaline. After another 15 minutes have passed the animals are placed into a cylindrical chamber of 2 liters capacity, exposed for 45 seconds to an aqueous histamine aerosol (1.25%), and subsequently the mortality is evaluated.

Evaluation: The mortality is plotted against the logarithm of the dose, and the $LD_{50}$ is determined according to J. Litchfield and F. Wilcoxon (J. Pharmacol. exp. Therap. 96, 99–113, 1949). With the $LD_{50}$ from this test and the cardiac $ED_{50}$ from the isoprenaline tachycardia inhibition test (anesthetized guinea pigs) a selectivity quotient $LD_{50}/ED_{50}$ is formed. A substance is considered to be cardioselective if the quotient is larger than 1.

Particularly effective are those compounds of the formula I in which $R_3$ and $R_4$ are methyl, i.e. substituted p-acylamino-1-phenoxy-3-(2-methyl-butinyl-3-amino-2)-2-propanols. Especially effective is 1-(2-cyano-4-isobutyroyl-amino)-phenoxy-3-(2-methylbutinyl-3-amino-2)-2-propanol; compared to acebutolol this compound exhibits an about 20 times stronger isoprenaline-antagonistic activity.

For pharmaceutical purposes the compounds of the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups and the like. One effective oral dosage unit of the compounds according to the present invention is from 0.013 to 4.0 mgm/kg body weight, preferably 0.06 to 1.33 mgm/kg body weight. The parenteral dosage unit range is 0.013 to 0.26 mgm/kg.

The following examples illustrate a few pharmaceutical dosage unit compositions comprising a compound of the present invention as an active ingredient and represent the best modes contemplated of using the invention.

EXAMPLE 8

Tablets

| | |
|---|---|
| 1-(2-Cyano-4-isobutyroylamino-phenoxy)-3-(2-methylbutinyl-3-amino-2)-2-propanol | 40.0 mgm |
| Corn starch | 164.0 mgm |
| Sec. calcium phosphate | 240.0 mgm |
| Magnesium stearate | 1.0 mgm |
| | 445.0 mgm |

Production:

The individual components are admixed thoroughly, and the mixture is granulated in the conventional way. The granulate is compressed into 445 mgm tablets, each containing 40 mgm of the active ingredient.

EXAMPLE 9

Gelatine capsules

The contents of the capsules are compounded from the following ingredients:

| | |
|---|---|
| 1-(2-Cyano-4-isobutyroylamino-phenoxy)-3-(2-methylbutinyl-3-amino-2)-2-propanol | 25.0 mgm |
| Corn starch | 175.0 mgm |
| | 200.0 mgm |

Production:

The ingredients are admixed thoroughly, and 200 mgm portions of the mixture are filled into gelatin capsules of suitable size. Each capsule contains 25 mgm of the active substance.

EXAMPLE 10

Injection solution

The solution is compounded from the following ingredients:

| | |
|---|---|
| 1-(2-Cyano-4-n-propionylamino-phenoxy)-3-(2-methylbutinyl-3-amino-2)-2-propanol | 2.5 parts |
| Sodium salt of EDTA (ethylene diamine tetraacetic acid) | 0.2 parts |
| Distilled water q.s. ad | 100.0 parts |

Production:

The active ingredient and the EDTA salt are dissolved in sufficient water, and the solution is diluted with water to the desired volume. The solution is filtered until free from suspended particles and filled into 1 ccm ampules under aseptic conditions. Finally, the ampules are sterilized and sealed. Each ampule contains 25 mgm of the active ingredient.

EXAMPLE 11

Coated sustained release tablets

| Core: | |
|---|---|
| (−)-1-(2-Cyano-4-isobutyroyl-phenoxy)-3-(2-methylbutinyl-3-amino-2)-2-propanol | 25.0 gm |
| Carboxymethylcellulose (CMC) | 295.0 gm |
| Stearic acid | 20.0 gm |
| Cellulose acetate phthalate (CAP) | 40.0 gm |
| | 380.0 gm |

Production:

The active ingredient, the CMC and stearic acid are thoroughly admixed, and the mixture is granulated in the conventional way, using a solution of the CAP in 200 ml of a mixture of ethanol and ethyl acetate. Then the granulate is compressed into 380 mgm cores, which are subsequently coated in the conventional way with a sugarcontaining 5% solution of polyvinyl pyrrolidone in water. Each coated tablet contains 25 mgm of the active ingredient.

EXAMPLE 12

Tablets

| | |
|---|---|
| 1-(2-Cyano-4-isobutyroylamino-phenoxy)-3-(3-ethylpentinyl-4-amino-3)-2-propanol | 35.0 gm |
| 2,6-Bis-(diethanolamino)-4,8-dipiperidino-pyrimido-[5,4-d]-pyrimidine | 75.0 gm |
| Lactose | 164.0 gm |

-continued

| Corn starch | 194.0 gm |
|---|---|
| Colloidal silicic acid | 14.0 gm |
| Polyvinyl pyrrolidone | 6.0 gm |
| Magnesium stearate | 2.0 gm |
| Soluble starch | 10.0 gm |
| Total | 500.0 gm |

Production:

The active ingredient is granulated as usual together with lactose, corn starch, colloidal silicic acid and polyvinyl pyrrolidone after admixing same thoroughly using an aqueous solution of the soluble starch. The granulate is admixed with the magnesium stearate and compressed into 500 mgm tablets, each of which contains 35 mgm of the first and 75 mgm of the second active ingredient.

Any one of the other compounds embraced by formula I or a non-toxic, pharmacologically acceptable acid addition salt thereof may be substituted for the particular active ingredient in Examples 8 through 11. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

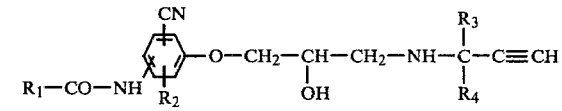

wherein $R_1$ is ethyl or isopropyl;

$R_2$ is hydrogen, halogen, alkyl of 1 to 4 carbon atoms, alkoxy of 1 to 4 carbon atoms or a bivalent radical —CH=CH—CH=CH— or —(CH$_2$)$_n$—, where n is an integer from 3 to 5, inclusive, and the free bonds of said bivalent radical are attached to adjacent carbon atoms of the phenyl ring; and $R_3$ is hydrogen or alkyl or 1 to 3 carbon atoms;

$R_4$ is alkyl of 1 to 3 carbon atoms; or $R_3$ and $R_4$, together with each other, are —(CH$_2$)$_p$—, where p is an integer from 4 to 6, inclusive, or a non-toxic, pharmacologically acceptable acid addition salt thereof.

2. A compound of claim 1, where $R_3$ and $R_4$ are both methyl.

3. A compound of claim 1, which is 1-(2-cyano-4-isobutyroyl-phenoxy)-3-(2-methyl-butinyl-3-amino)-2-propanol or a non-toxic, pharmacologically acceptable acid addition salt thereof.

4. A β-adrenolytic pharmaceutical dosage unit composition consisting essentially of an inert pharmaceutical carrier and an effective β-adrenolytic amount of a compound of claim 1.

5. A method for the treatment and prophylaxis of diseases of the coronaries, for the treatment of hypertension, or for the treatment of cardiac arrhythmia, which comprises administering to a warm-blooded animal or human an effective amount of a compound of claim 1.

6. The method of claim 1 for the treatment of tachycardia.

* * * * *

UNITED STATES PATENT AND TRADEMARK OFFICE
CERTIFICATE OF CORRECTION

PATENT NO. : 4,344,964
DATED : August 17, 1982
INVENTOR(S) : HERBERT KÖPPE ET AL.

It is certified that error appears in the above—identified patent and that said Letters Patent is hereby corrected as shown below:

Column 3, line 64: "10 of" should be -- 10 ml of --.

Column 6, line 54: "by" should be -- By --.

Column 10, line 15: "or", second occurrence, should be -- of --.

Signed and Sealed this

Twenty-fifth Day of January 1983

[SEAL]

Attest:

GERALD J. MOSSINGHOFF

Attesting Officer

Commissioner of Patents and Trademarks